United States Patent [19]
Bellasio

[11] Patent Number: 5,777,125
[45] Date of Patent: Jul. 7, 1998

[54] PROCESS FOR THE PREPARATION OF TERTIARY CARBINOLS CONTAINING AN AMINO SUBSTITUENT

[75] Inventor: Elvio Bellasio, Como, Italy

[73] Assignee: Gruppo Lepetit SpA, Gerenzano, Italy

[21] Appl. No.: 449,027

[22] Filed: May 24, 1995

Related U.S. Application Data

[63] Continuation of Ser. No. 351,898, Dec. 8, 1994, abandoned, which is a continuation of Ser. No. 270,102, Jul. 1, 1994, abandoned, which is a continuation of Ser. No. 146,773, Nov. 1, 1993, abandoned, which is a continuation of Ser. No. 60,883, May 12, 1993, abandoned, which is a continuation of Ser. No. 989,997, Dec. 10, 1992, abandoned, which is a continuation of Ser. No. 821,266, Jan. 10, 1992, abandoned, which is a continuation of Ser. No. 644,756, Jan. 24, 1991, abandoned, which is a continuation of Ser. No. 317,414, Mar. 1, 1989, abandoned.

[30] Foreign Application Priority Data

Mar. 3, 1988 [GB] United Kingdom ............... 8805113

[51] Int. Cl.$^6$ ............... C07B 49/00; C07D 211/22
[52] U.S. Cl. ............... 546/241; 540/450; 540/609; 548/570; 549/435; 564/320
[58] Field of Search ............... 546/241; 564/320

[56] References Cited

U.S. PATENT DOCUMENTS

| | | | |
|---|---|---|---|
| 2,624,739 | 1/1953 | Werner et al. | 546/241 |
| 2,804,422 | 8/1957 | Schumann et al. | 514/317 |
| 2,832,786 | 4/1958 | Tilford et al. | 546/21 |
| 2,833,775 | 5/1958 | Sperber et al. | 546/241 |
| 2,879,294 | 3/1959 | Campbell | 564/320 |
| 3,000,896 | 9/1961 | Hoffman et al. | 546/241 |
| 3,052,685 | 9/1962 | Weston | 546/241 |

FOREIGN PATENT DOCUMENTS

| | | |
|---|---|---|
| 0065847 | 6/1981 | Japan . |
| 0805511 | 12/1958 | United Kingdom . |

OTHER PUBLICATIONS

Sumitomo Chemical Co., Ltd, Chemical Abstracts, vol. 95: 203530g (1981).
Mark, "Advanced Org Chem 4th Edition" (John Wiley & Sons, 1992, p. 273).

J. Greenstein, "Chemistry of Amino Acids" vol. 1 pp. 446–447 (1984).

Morrison & Boyd, "Organic Chemistry, 6th Edition" (1992) p. 740.

Seyhan N. Ege, The University of Michigan, Organic Chemistry Second Edition, pp. 590–591, (1989)

Sumitomo Chemical Co., Ltd. (Derwent Abstr. B05 E16 E14) "Optically active aromatic alcohol cpds. prepn. –by treating optically active alpha–amonacid with benzl magnesium halide". (1981).

Japanese Patent Application No. 7630 (1958), (Chem. Abstr. 54, 2365g) 1960.

Japanese Patent Application No. 7269 (1958), (Chem. Abstr. 54, 2365f) 1960.

Japanese Patent Application No. 930 (1958), (Chem. Abstr. 53, 1384c) (1958).

Danish 86, 139, Chemical Abstracts, vol. 53, 11415d (1958).

Nutzel et al., "Metallorganische Verbindungen," vol. XIII/2a, 1973, pp. 251–253, Georg Thieme Verlag Stuttgart, DE.

Sumitomo Chem., Chemical Abstracts 95:203530g.

Thomas et al., Chemical Abstracts, vol. 19, No. 1, 10th Jan. 1925, p. 635, Columbus, Ohio, US: 'The Action of the Grignard reagent on amino acids,' Z. Phisiol. Chem. 140, 244–60 (1924).

*Primary Examiner*—Mark L. Berch
*Attorney, Agent, or Firm*—Ruth E. Homan

[57] ABSTRACT

A process for the preparation of tertiary diphenyl carbinols containing a primary or secondary amine substituent on the aliphatic moiety attached to the carbinol function which consists in contacting a Grignard phenyl reagent with an aminoacid wherein the mobile protons are not masked in an aprotic inert organic solvent or a mixture thereof at a temperature between 20° C. and the boiling temperature by the reaction mixture.

The reaction products are useful as active ingredients of medicaments and intermediates for the manufacture thereof.

9 Claims, No Drawings

PROCESS FOR THE PREPARATION OF TERTIARY CARBINOLS CONTAINING AN AMINO SUBSTITUENT

This is a continuation of application Ser. No. 08/351,898, filed Dec. 8, 1994 abandoned, which is a continuation of application Ser. No. 08/270,102, filed Jul. 1, 1994, now abandoned, which is a continuation of application Ser. No. 08/146,773, filed Nov. 1, 1993, now abandoned, which is a continuation of application Ser. No. 08/060,883 filed May 12, 1993, now abandoned, which is a continuation of application Ser. No. 07/989,997 filed Dec. 10, 1992, now abandoned, which is a continuation of application Ser. No. 07/821,266, filed Jan. 10, 1992, now abandoned, which is a continuation of application Ser. No. 07/644,756, filed Jan. 24, 1991, now abandoned, which is continuation of application Ser. No. 07/317,414, filed Mar. 1, 1989, now abandoned, which is herein incorporated by reference.

The process of this invention regards the production of tertiary diphenyl carbinols of the formula

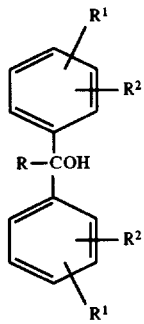

wherein

R is an amino substituted alkyl whose alkyl moiety is a linear or branched aliphatic chain of 1 to 6 carbon atoms and the aminic substituent is a group $NHR^3$ attached to one of the carbon atoms of the alkyl moiety wherein $R^3$ represents hydrogen, a linear or branched alkyl of 1 to 6 carbons, benzyl, phenylethyl, a linear or branched alkylene chain of 1 to 6 carbon atoms connecting the nitrogen atom with one of the carbons of the first alkyl moiety to form a nitrogen containing saturated heterocyclic ring of 5 to 8 members, $R^1$ and $R^2$ each independently represents hydrogen, $C_1$–$C_4$ linear or branched alkyl, $C_1$–$C_2$ alkoxy, fluoro, chloro, or, taken together, represent a methylenedioxy group.

and the acid addition salts thereof.

Representative examples of the alkyl moiety are: methyl, ethyl, propyl, isopropyl, butyl, sec.butyl, tert-butyl, isopentyl, neopentyl, tert-pentyl, 1,2-dimethylpropyl, hexyl, isohexyl, 1-methylpentyl, 2-methylpentyl, 3,3-dimethylbutyl, 1,2,2-trimethylpropyl and the like. According to the above definition, one of the carbon of said alkyl moieties must bear a grup $NHR^3$ as a substituent.

When the radical $R^3$ represents a linear or branched alkylene chain linked to one of the carbons of the first alkyl moiety as defined above, the first alkyl moiety has two substitutions and the alkylene chain, together with the nitrogen atom and the adjacent portion of the first alkyl moiety, forms a nitrogen containing saturated heterocyclic ring of 5 to 8 members such as pyrrolidine, piperidine, hexahydroazepine and octahydroazocine, which can optionally bear alkyl substituents on the carbon skeleton. The length and the number of the alkyl substituents on the carbon skeleton is correlated with the branching of either the portion of the first alkyl moiety or the alkylene chain.

Accordingly, representative examples of the amino substituted radical R represented in the formula I above are the following:

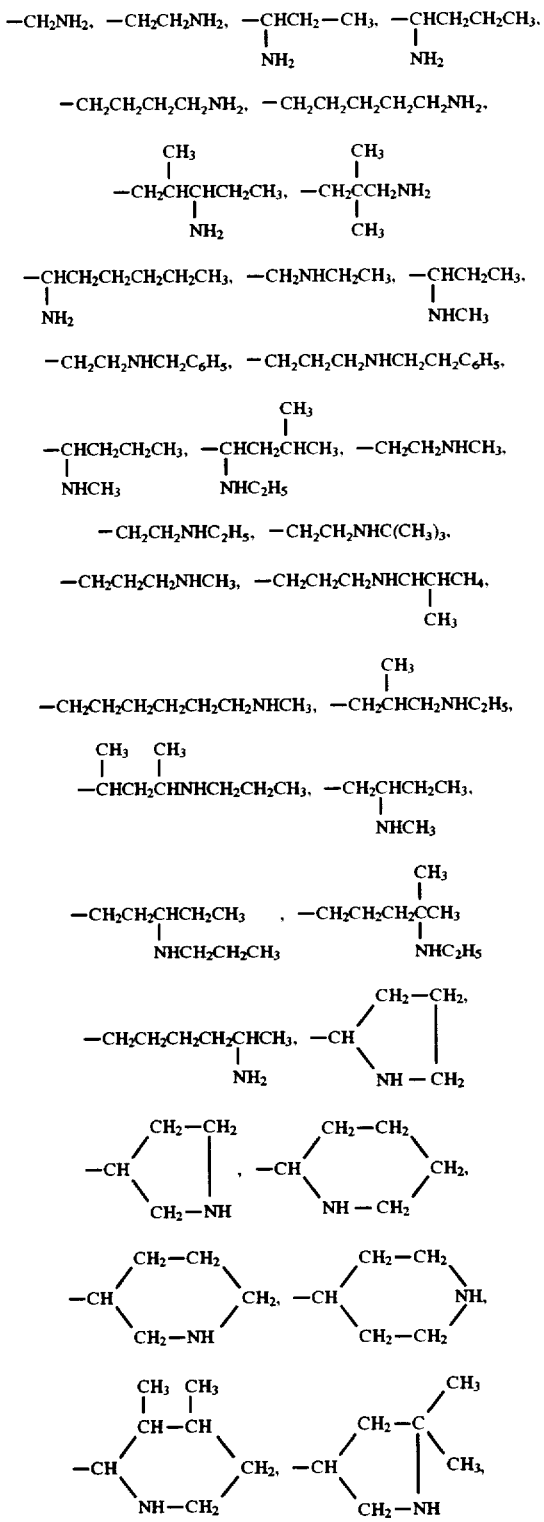

-continued

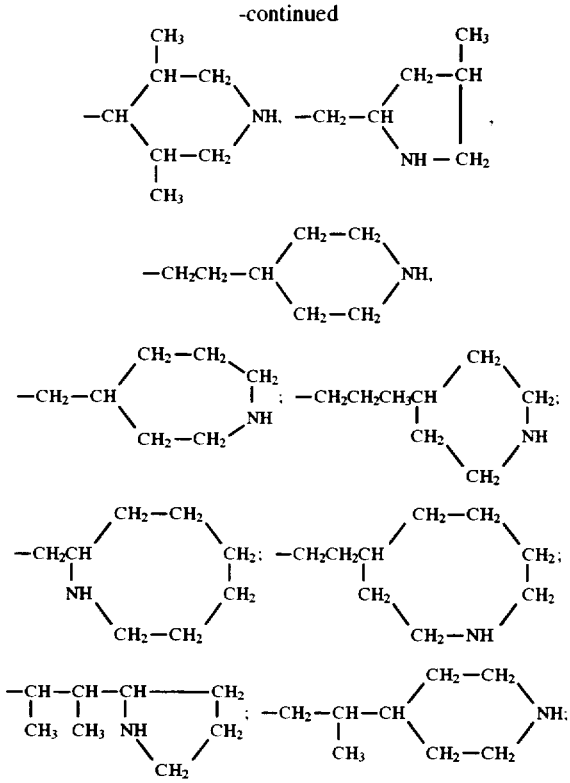

The compounds which can be obtained through this process are useful as active ingredients of medicaments and as intermediates for the manufacture thereof.

Among the active ingredients for medicaments and the intermediates for their production which can be obtained through this process are substances (or intermediates for the manufacture of substances) active on the central nervous system and as antihistaminics. Examples of said products and intermediates are described in U.S. Pat. No. 2,624,739, (C.A. 47, 11259) U.K. 805511 (C.A. 53, 12249) and U.S. Pat. No. 2,804,422, (C.A. 53, 1558).

The acid addition salts of the compounds which can be obtained through the process of this invention are all type of acid addition salts with the amine moiety. Therefore, examples of such salts are those with acids which are currently used in the industrial synthetic processes for the isolation of intermediates or final active substances bearing an amino group.

Representative and suitable acid addition salts of the compounds of formula (I) include those salts formed by standard reactions with both organic and inorganic acids such as, for example, hydrochloric, hydrobromic, sulfuric, phosphoric, acetic, trifluoroacetic, trichloroacetic, succinic, citric, ascorbic, lactic, maleic, fumaric, palmitic, cholic, pamoic, mucic, glutamic, camphoric, glutaric, glycolic, phthalic, tartaric, lauric, stearic, salicylic, methanesulfonic, ethanesulfonic, benzenesulfonic, sorbic, picric, benzoic, cinnamic and the like.

A preferred group of acid addition salts of the compounds of formula (I) are the salts with the anion which are pharmaceutically acceptable, i.e., which can be employed in the pharmaceutical use of the compounds.

Representative examples of such acids are hydrochloric, hydrobromic, sulfuric, lactic, maleic, succinic, fumaric, glutaric, citric, malic, p-toluenesulfonic, methanesulfonic, tartaric acid and the like.

The present invention provides a process for preparing the tertiary diphenyl carbinols containing an aminic substituent of formula (I) above characterized in that a free acid of the formula R—COOH is contacted with a Grignard reagent of the formula

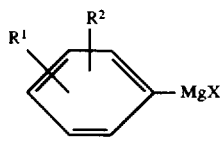

wherein

R. $R^1$ and $R^2$ have the same meanings as above and X represents chloro or bromo in an aprotic inert organic solvent or a mixture thereof at a temperature between 20° C. and the boiling temperature of the reaction mixture.

A variety of methods for preparing carbinols of the above general formula I is disclosed in the prior art. For instance, U.S. Pat. No. 2,624,739, (C.A. 47, 11259) U.S. Pat. No. 2,804,422 (C.A. 52, 1558) and U.S. Pat. No. 3,052,685 (C.A. 58, 512) disclose processes for the preparation of diphenyl-piperidyl-carbinol compounds based on catalytic hydrogenation of the corresponding diphenyl-pyridyl-carbinol derivatives. Danish patent 86.139 (C.A. 53, 11415) describes the same type of process wherein the hydrogenation of the pyridine rest is carried out through electrolysis.

Japanese patent application 7630/58 (Chemical Abstracts, 54, 2365) teaches the preparation of the same type of compounds by reaction of phenylmagnesium bromide with ethyl-N-benzylisonipecotinate followed by catalytic de-benzylation according to Japanese patent application 930/58.

Diphenyl-piperidyl-carbinols are prepared by reaction of lower alkyl esters of N-protected isonipecotic acids with phenylmagnesium bromide followed by hydrolysis of the N-protecting group according to U.S. Pat. No. 3,000,896 (C.A 56, 2439).

1,1-Diaryl-2-aminoalkanols falling within the general formula I are prepared by reaction of phenyl-magnesium bromide with 2-amino-hexanoic acid ethyl ester (U.K. 805,511; C.A. 53, 12249).

As it is apparent from the above mentioned prior-art, when the Grignard reagents are employed to produce tertiary carbinols containing aminic substituents from the corresponding acids, both the carboxylic and aminic functions are masked by replacement of the mobile hydrogen atoms.

A particular feature of the process of this invention is that it provides very high yields and it does not involve any replacement of the mobile protons of either the carboxylic function and/or the aminic moiety of the reaction substrate R—COOH through formation of masking ester or amide bonds.

Both the economical and the operative aspects of the manufacture of the tertiary diphenyl carbinols are therefore favorably affected by the typical feature of the process of this invention. In fact, the preparation of starting materials such as the aminoacid masked in the amino and/or carboxylic moiety is a troublesome and costly operation. Moreover, the separation of the final diphenyl carbinols from the reaction products and the recovery of the solvent(s) require the adoption of more complicated and expensive procedures when the final reaction mixture contains also side-products deriving from the decomposition of the ester and/or amide functions.

According to a general way to carry out the process of this invention, the phenylmagnesium reagents are prepared through common techniques indicated in general text books.

such as, for instance: "Methoden der Organischen Chemie", 4th Edition, Vol. XIII/2a, Georg Thieme Verlag, Stuttgart. The solvent systems which are used for preparing the Grignard reagents are those usually employed in the art and include lower alkyl ethers, dimethoxymethane, 1,1-dimethoxyethane, 1,2-dimethoxyethane, cyclic ethers like tetrahydrofuran, tetrahydropyran, dioxane, and inert aromatic hydrocarbons such as benzene, toluene and xylene or a mixture thereof. The Grignard reagent is usually employed in an amount of 4 to 6 molecular proportions (molar equivalents) for each molecular proportion of the acid of the formula R—COOH.

The aminoacid R—COOH is added to the Grignard reagent solution or suspension as such or, if it is a solid, preferably, as a ground powder or a suspension thereof in an inert aprotic solvent which is mixable with that (those) employed for the preparation of the Grignard reagent. Usually, the solvent for suspending the aminoacid R—COOH is selected among those which are mentioned above for the preparation of the Grignard reagents. Tetrahydrofuran or mixtures of tetrahydrofuran and toluene are the preferred solvents suitable for both the manufacture of the Grignard reagent and the suspension of the aminoacid for the reaction process of this invention.

The addition of the aminoacid is generally made by keeping the temperature of the reaction mixture between 20° C. and 100° C. When the addition is completed, the mixture is heated for 12 to 25 hours at a temperature between 70° C. and the boiling temperature of the mixture, preferably between 80° C. and 120° C., under stirring.

In certain cases an over-pressure of 0.2 to 2.0 atmospheres (atmospheres above atmospheric pressure) is created, for instance, by introducing inert gas (e.g. nitrogen) into the reaction vassel, in order to maintain the reaction temperature at the highest values of the above mentioned preferred range. When the reaction is carried out at a pressure higher than the atmospheric pressure, the reaction time may be shorter than the interval indicated above, for instance it may vary from 6 to 12 hours.

The amount of the solvent or mixture of solvents (and, in this latter case, their mutual proportions) used to carry out the process of the invention, in general depends on the operative conditions. If the same solvent or mixture of solvents is employed for both the manufacture of the Grignard reagent and the suspension of the aminoacid, in general, it is preferred to have a reaction solvent volume corresponding to from about 5 to about 20 ml of solvent or mixture of solvents for each gram of aminoacid, with the lower amounts of the above range being usually employed when the reaction is carried out under an over-pressure as indicated above.

With regard to the mutual proportions of the solvents when a mixture thereof is employed, usually, they may vary within a wide range depending on the specific characteristics of each solvent. In general, with the mixtures tetrahydrofuran: toluene mentioned above, the proportions may vary from 10:1 to 1:10 preferably from 3:1 to 1:3.

When the reaction is completed, the reaction mixture is poured into an excess of water while concentrate mineral acid (e.g. hydrochloric acid) is added thereto by keeping the pH between 1 and 2.5. The temperature during the addition is kept between 0° C. and 60° C. The mineral acid addition salt of the amino substituted carbinol of formula (I) is recovered from the exhausted reaction mixture through usual separation techniques which, in most cases, consist in the filtration or centrifugation of the precipitated mineral acid addition salt.

The recovered product is further washed with water or is transformed into a non-salt form or into an acid addition salt with another acid by common procedures.

The following examples illustrate the invention without limiting its scope.

EXAMPLE 1

Preparation of diphenyl-4-piperidyl carbinol hydrochloride

In a 6000 ml round bottomed flask equipped with mechanical stirrer on an oil bath, the following materials are charged: magnesium turnings (188 g), tetrahydrofuran (863 ml), chlorobenzene (56.8 g), and a small amount of phenylmagnesium chloride reagent of a previous preparation (37 g).

The mixture is heated to reflux while stirring and as soon as the reaction is started a solution of chlorobenzene (821.1 g) and toluene (961 ml) is slowly added at such a rate so as to maintain reflux. When the addition is complete the mixture is refluxed until magnesium is almost completely dissolved. Then, isonipecotic acid (200 g) and toluene (400 ml) are added to the Grignard reagent kept at a temperature between 20° C. and 100° C.

The mixture is heated at reflux for a period of 15 to 17 hours, then it is slowly poured into 6–8 liters of cold water. At the same time, concentrated hydrochloric acid (33–36%) is slowly added to the water in order to maintain the pH between 1.5 and 2.5.

The temperature during the addition is maintained between 0° C. and 20° C.

When the addition is completed the suspension is stirred for 2–4 hours at 15° C.–20° C., then it is filtered and the product of the title is washed with water and dried in vacuo (about 0.1 atm) at 80°–90° C. Yield 408 g (87% molar).

EXAMPLE 2

Preparation of di-(p.tolyl)-4-piperidyl carbinol hydrochloride

In a 3 l round bottomed flask equipped with mechanical stirrer on an oil bath, the following materials are charged: magnesium turnings (48.64 g), tetrahydrofuran (226 ml) and a small crystal of iodine. Then the mixture is heated while a solution of 4-chlorotoluene (253.18 g) and toluene (453 ml) is slowly added within 2 h. At 70° C. the Grignard reaction starts and at the end of the addition of chlorotoluene the temperature reaches 105° C. The mixture is then heated at the reflux temperature until magnesium is almost completely dissolved. After cooling to 100° C. isonipecotic acid (51.68 g) is added and the suspension is refluxed for 16 h. Then, the mixture is slowly poured into water (1333 ml) while stirring. Concentrated hydrochloric acid is also slowly added in order to maintain the pH between 1 and 2. The temperature is maintained below 20° C. with external cooling.

Then the mixture is stirred for 3 h, the insoluble material is collected by suction filtration, washed with water (3×250 ml) and dried in vacuo at 90° C. Yield: 113 g (85% molar).

EXAMPLE 3

Preparation of diphenyl-4-piperidyl carbinol hydrochloride.

In a 8 liter stainless steel reactor equipped with mechanical stirrer and a steam bath the following materials are charged: magnesium turnings (188 g), tetrahydrofuran (863 ml), chlorobenzene (56.8 g), and a small amount of phenylmagnesium chloride reagent of a previous preparation (37 g). The mixture is heated to reflux while stirring and as soon as the reaction is started a solution of chlorobenzene (821.1 g) is slowly added at such a rate so as to maintain reflux. When the addition is complete the mixture is refluxed until magnesium is almost completely dissolved. Then isonipecotic acid (200 g) and toluene (300 ml) are added to the Grignard reagent kept at 50° C. The mixture is heated at reflux at atmospheric pressure for about 1 hour. Then, the reaction is put under pressure with nitrogen (0.4 to 1.5 atm) and the mixture is heated between 105° and 120° C. for 10 hrs. After this, the reaction mixture is cooled, the pressure of the reaction is slowly decreased and the mixture is slowly poured into 4 liter of cold water. Then it is worked as in the last part of Example 1. Yield 415 g of the compound of the title.

I claim:

1. A process for the manufacture of tertiary diphenyl carbinols of the formula (I) Formula I

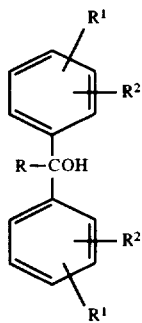

wherein,
a) R is 4-piperidinyl, $R^1$ and $R^2$ are both hydrogen or
b) R is 4-piperidinyl, $R^1$ is hydrogen and $R^2$ is a methyl in a para position to the phenyl ring, and the acid addition salts thereof characterized in that one mole of free acid of the formula R—COOH is added to an amount of four to six moles of a Grignard reagent of the formula

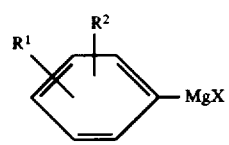

wherein,

R, $R^1$, and $R^2$, have the same meanings as above and X represents chloro or bromo in a mixture of tetrahydrofuran and toluene and during the addition of the acid the temperature of the reaction mixture is kept between 20° and 100° C. and, when the addition is complete the reaction mixture is heated under atmospheric pressure at a temperature between 70° C. and the boiling temperature of the mixture for a period of 12 to 25 hours, or alternately , the reaction mixture is heated under a pressure of from 0.2 to 2.0 atmospheres above atmospheric pressure at a temperature between 80° and 120° C. for a period of 6 to 12 hours and then the reaction mixture is poured into an excess of water while adding and excess of concentrated mineral acid thereby keeping the pH between 1 and 2.5, and additionally, transforming the so obtained mineral acid addition salt of the compound of Formula I into a non-salt form or into another acid addition salt.

2. A process as in claim 1 wherein the tertiary diphenyl carbinol is in the form of an acid addition salt selected from the group consisting of hydrochloric, hydrobromic, sulfuric, lactic, maleic, succinic, fumaric, glutaric, citric, malic, p-toluenesulfonic, methanesulfonic and tartaric acid.

3. A process as in claim 1 in which the reaction mixture is heated under pressure of from 0.4 to 1.5 atmospheres above atmospheric pressure at a temperature between 105° and 120° C.

4. A process as in claim 1 wherein the carbinol of formula (I) is diphenyl-4-piperdyl carbinol.

5. A process as in claim 2 wherein R is 4-piperidyl, $R^1$ and $R^2$ are both hydrogen and the acid addition salt is the hydrochloride.

6. A process as in claim 2 wherein R is 4-piperidyl, $R^1$ is hydrogen and $R^2$ is methyl in para-position of the phenyl ring and the acid addition salt is the hydrochloride.

7. A process as in claim 1 wherein the mineral acid is hydrochloric acid.

8. A process as in claim 1 or 7 wherein the tetrahydrofuran/toluene ratio is from 10:1 to 1:10.

9. A process as in claim 1 or 7 wherein the tetrahydrofuran/toluene ratio is from 3:1 to 1:3.

* * * * *